(12) United States Patent
Neetz

(10) Patent No.: US 10,073,946 B2
(45) Date of Patent: Sep. 11, 2018

(54) METHOD FOR GENERATING A MANUFACTURING MODEL FOR A MEDICAL IMPLANT

(71) Applicant: Siemens Aktiengesellschaft, München (DE)

(72) Inventor: Manuel Neetz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 312 days.

(21) Appl. No.: 15/007,649

(22) Filed: Jan. 27, 2016

(65) Prior Publication Data

US 2016/0231732 A1 Aug. 11, 2016

(30) Foreign Application Priority Data

Feb. 10, 2015 (DE) .................. 10 2015 202 286

(51) Int. Cl.
*G05B 19/4097* (2006.01)
*G06F 19/00* (2018.01)

(52) U.S. Cl.
CPC .. *G06F 19/321* (2013.01); *G05B 2219/32104* (2013.01)

(58) Field of Classification Search
CPC ........ G06F 19/321; G06F 19/12; G06F 17/50; G06F 17/5009; G06F 19/3406; G06F 19/345; G16H 50/50; G16H 10/60; G16H 50/30; G06T 2207/10081; G06T 2207/10088; G06T 2207/30012;

(Continued)

(56) References Cited

U.S. PATENT DOCUMENTS 5,398,684 A 3/1995 Hardy
8,483,469 B2 * 7/2013 Pavlovskaia ............. G06K 9/32
382/131

(Continued)

FOREIGN PATENT DOCUMENTS

CN 1938708 A 3/2007
CN 102164564 A 8/2011

(Continued)

OTHER PUBLICATIONS

German Office Action dated May 3, 2016.

(Continued)

*Primary Examiner* — Jonathan Han
(74) *Attorney, Agent, or Firm* — Harness, Dickey & Pierce, P.L.C.

(57) ABSTRACT

A method is disclosed for generating a manufacturing model for a medical implant. In the method, image data of a body region is provided, and regions corresponding to structures of different tissue are segmented; a shape of the implant is defined on the basis of the regions corresponding to the structures and an interaction with the implant is determined for at least one structure in a patient-specific manner on the basis of the image data; for a number of structures, the respective interaction with the implant is checked for an exceedance of a critical stress; and the shape of the implant is defined as a manufacturing model. The manufacturing model is then stored on a non-transitory data carrier and/or output via an interface if the critical stress is not exceeded for any checked interaction of the implant with the respective structure.

19 Claims, 4 Drawing Sheets

(58) Field of Classification Search
CPC ......... G06T 2207/30196; G06T 7/0014; G06T
2207/30008; G06T 7/11; G06T 7/0012;
G06T 17/20; G06T 2200/04; G06T
2200/08; G06T 17/00; G06T 19/00; G06T
2210/41; G05B 2219/32104; A61B
2034/102; A61B 2034/108; A61B 34/10
USPC ................................................ 700/118; 705/3
See application file for complete search history.

(56) References Cited

U.S. PATENT DOCUMENTS

| | | | | |
|---|---|---|---|---|
| 8,737,700 | B2* | 5/2014 | Park | A61B 5/055 |
| | | | | 382/128 |
| 8,777,875 | B2* | 7/2014 | Park | A61B 17/15 |
| | | | | 600/587 |
| 2005/0216314 | A1 | 9/2005 | Secor | |
| 2007/0050074 | A1 | 3/2007 | Holzner et al. | |
| 2010/0023015 | A1 | 1/2010 | Park | |
| 2010/0256479 | A1 | 10/2010 | Park et al. | |
| 2010/0292963 | A1* | 11/2010 | Schroeder | A61F 2/30 |
| | | | | 703/1 |
| 2013/0039551 | A1 | 2/2013 | Pavlovskaia et al. | |
| 2013/0132054 | A1 | 5/2013 | Sharma et al. | |
| 2013/0282351 | A1 | 10/2013 | Tank | |
| 2014/0324205 | A1 | 10/2014 | Park et al. | |

FOREIGN PATENT DOCUMENTS

| | | |
|---|---|---|
| CN | 104081401 A | 10/2014 |
| DE | 102005013722 A1 | 9/2006 |
| DE | 102005035475 A1 | 5/2007 |
| DE | 102006059829 A1 | 6/2008 |
| DE | 102011008074 A1 | 7/2012 |
| WO | WO 2004110309 A2 | 12/2004 |
| WO | WO 2007008289 A2 | 1/2007 |
| WO | WO 2012044997 A2 | 4/2012 |
| WO | WO 2014036551 A1 | 3/2014 |

OTHER PUBLICATIONS

Chinese Office Action and English translation thereof dated Jun. 1, 2017.
German Office Action dated Dec. 9, 2016.
Chinese Office Action dated Apr. 11, 2018 for CN Application No. 2016100592198.

* cited by examiner

METHOD FOR GENERATING A MANUFACTURING MODEL FOR A MEDICAL IMPLANT

PRIORITY STATEMENT

The present application hereby claims priority under 35 U.S.C. § 119 to German patent application number DE 102015202286.2 filed Feb. 10, 2015, the entire contents of which are hereby incorporated herein by reference.

FIELD

At least one embodiment of the invention generally relates to a method for generating a manufacturing model for a medical implant, wherein image data of a body region is provided, regions are segmented in the image data, the regions corresponding in each case to structures of different tissue, and wherein a shape of the implant is defined on the basis of the regions which correspond to the structures.

BACKGROUND

It is desirable for the production of a medical implant, with as high a level of automation as possible for high efficiency, nevertheless to achieve the best possible adjustment to the individual conditions of the anatomy of the relevant patient, which a priori challenges complete automation of the manufacturing process. The desire for a patient-specific anatomical adaptation thus applies here to different implants such as bone implants, an intervertebral disk replacement or cartilage structures for plastic or reconstructive surgery.

Particularly with an implant which, on account of an interaction, for instance as a result of movements, with one or a number of adjacent tissue structures is exposed to a constant stress, a detailed patient-specific adjustment of the implant to the surrounding tissue can prevent wear of the implant due to the stress. Similarly, unwanted reactions by the implant to the tissue structures involved in the interaction can also be reduced here, which helps with preventing inflammations, degeneration, sclerosis and physical wear responses of the tissue structures as a result of the implant.

WO 2004/110309 discloses a method, which, for the manufacture of an implant, first records three-dimensional tomographic image data of the body region for which the implant is provided, and on the basis of this image data of the body region creates a manufacturing model of the implant. The implant is then produced on the basis of the manufacturing model created based on the tomographic image data. WO 2014/036551 discloses a method for the patient-specific embodiment of an implant, which uses three-dimensional tomographic image data in particular to determine two-dimensional contact surfaces of a bone implant with the bone for which the implant is intended.

However, with the cited methods the image data is generally only recorded with one modality, in other words for instance using computed tomography (CT) or magnetic resonance tomography (MRT), and a manufacturing model of the implant is then generated directly by way of this image data generated by one modality. In the generation of the manufacturing model, this then results in substantially only the anatomical structures of the relevant body region which are particularly effectively resolved by the modality used, in other words bone structures in CT or soft tissue structures in MRT, being taken into account.

Information relating to any damage to the structures which are less effectively resolved by the modality used in each case is therefore not actually available for the generation of the manufacturing model. Moreover, as a result of the static nature of the image data, possible anatomical changes to the relevant body region (for instance as a result of movements), which could affect the implant, are not taken into account during the adjustment of the implant, and nor is the stress on the implant that may be produced by such anatomical changes.

SUMMARY

At least one embodiment of the invention specifies a method for generating a manufacturing model for a medical implant, which enables as effective an adjustment of the implant to the patient-specific anatomical conditions of the tissue structures surrounding the implant as possible and in the process takes into account the long-term effects of the interactions of the implant and the surrounding tissue.

At least one embodiment of the invention is directed to a method for generating a manufacturing model for a medical implant, wherein image data of a body region is provided, regions which correspond in each case to structures of different tissue are segmented in the image data, a shape of the implant is defined on the basis of the regions which correspond to the structures, an interaction with the implant is determined in a patient-specific manner for at least one structure on the basis of the image data, the respective interaction with the implant checks for an exceedance of a predefined critical stress for a number of structures and the shape of the implant is defined as a manufacturing model, and the manufacturing model is stored on a non-transitory data carrier and/or output by way of an interface if the predefined critical stress is not exceeded for any checked interaction of the implant with the respective structure.

Advantageous and in part separately considered inventive embodiments of the inventions are presented in the claims and in the description which follows.

At least one embodiment of the invention further specifies an apparatus which is set up to perform the method described above for generating a manufacturing model. This comprises in particular a processor or computer, which can be configured in particular with at least one ASIC designed especially for this purpose. The advantages specified for the method and its developments can be analogously transferred to the apparatus.

At least one embodiment of the invention moreover specifies a computer program with program code for performing the method described above for generating a manufacturing model, when the computer program is run on a computer.

At least one embodiment of the invention moreover specifies a non-transitory computer readable medium including program code, for performing an embodiment of the method when the program code is executed on a computer.

At least one embodiment of the invention also specifies a method for producing a medical implant, which has method steps firstly comprising the generation of a manufacturing model via a method as described above, secondly the generation of a construction program which can be read by a producing apparatus on the basis of the manufacturing model and thirdly the generation of the implant in the producing apparatus on the basis of the construction program. One particular advantage here is that the manufacturing model can be output by the method for generation in a data format, which has a matrix-like three-dimensional volume representation of the implant, such as e.g. a CAD file.

Such a representation can be translated directly for a plurality of producing apparatuses, thus for instance for a 3D printer or a milling machine, into a construction program which can be read by the apparatus, which can comprise the instructions for the apparatus which are necessary for manufacture such as, in the case of the 3D printer, a file in the .stl format. A high probability of the manufacturing model output and a practical usability are thus ensured. Particularly with an output in an advantageous file format, the generation of the manufacturing model can be separated from the material production of the implant, which can contribute to simplifying the manufacture

BRIEF DESCRIPTION OF THE DRAWINGS

An example embodiment of the invention is explained in more detail below with reference to a drawing. Shown schematically in each case here are.

Parts and variables which correspond to one another are provided with the same reference numerals in all the figures.

DETAILED DESCRIPTION OF THE EXAMPLE EMBODIMENTS

Figure 1:
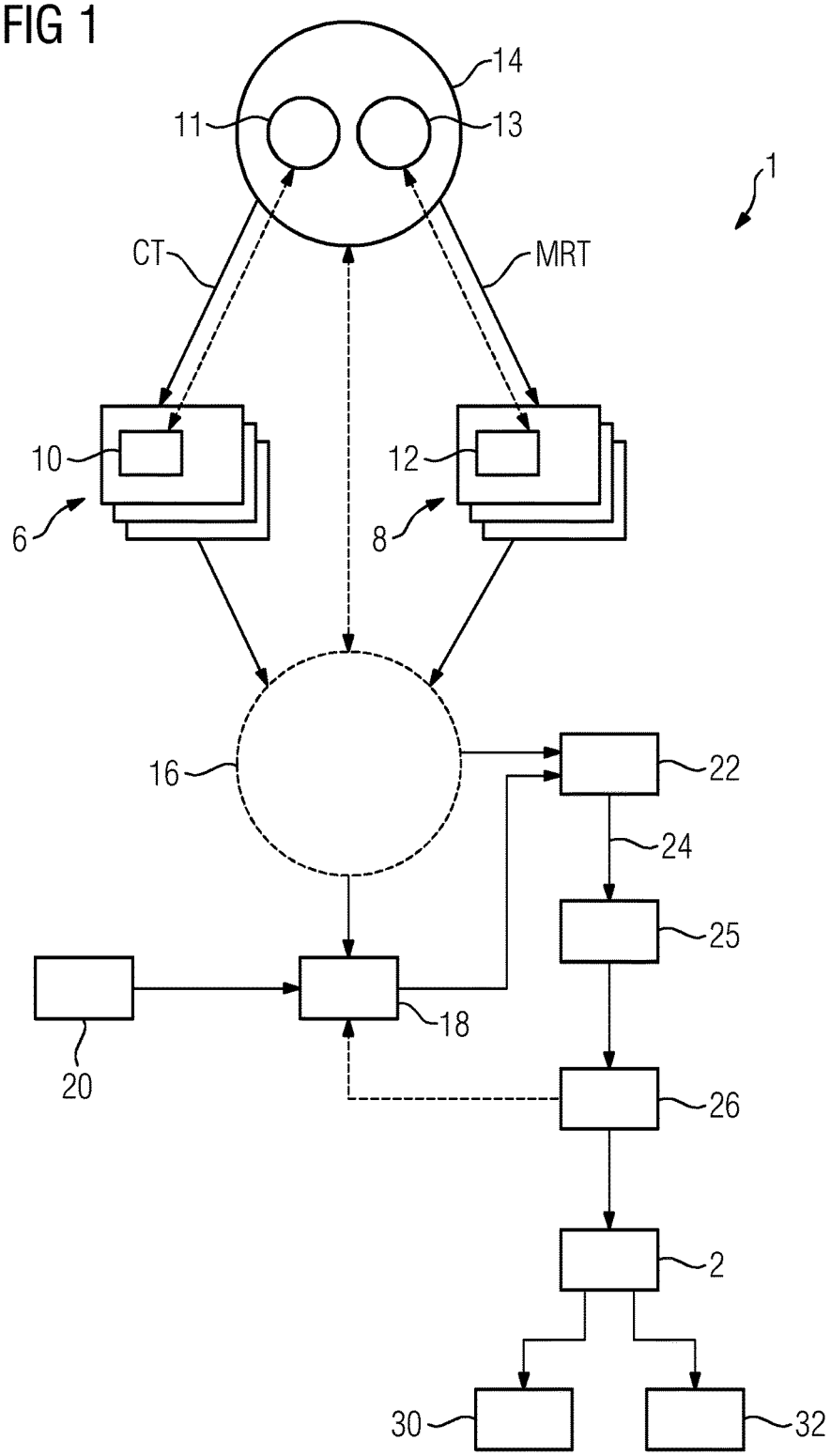
FIG. 1 a block diagram of the process flow of a method for generating a manufacturing model for a medical implant, FIG. 2 a block diagram of the process flow of a method for manufacturing a medical implant designed according to FIG. 1, FIG. 3 first image data of a body region of a spinal column, FIG. 4 second image data of a body region of a spinal column, FIG. 5 a longitudinal section of a simulation of an interaction of an implant with surrounding tissue based on the image data according to FIG. 3 and FIG. 4 and FIG. 6 a cross-sectional representation of a simulation of an interaction of a cardiac valve implant with the surrounding tissue.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

At least one embodiment of the invention is directed to a method for generating a manufacturing model for a medical implant, wherein image data of a body region is provided, regions which correspond in each case to structures of different tissue are segmented in the image data, a shape of the implant is defined on the basis of the regions which correspond to the structures, an interaction with the implant is determined in a patient-specific manner for at least one structure on the basis of the image data, the respective interaction with the implant checks for an exceedance of a predefined critical stress for a number of structures and the shape of the implant is defined as a manufacturing model, and the manufacturing model is stored on a non-transitory data carrier and/or output by way of an interface if the predefined critical stress is not exceeded for any checked interaction of the implant with the respective structure.

Advantageous and in part separately considered inventive embodiments of the inventions are presented in the claims and in the description which follows.

An embodiment of the method is preferably to be performed here by a computer, which has a data connection with a non-transitory data carrier and/or an interface. Image data of the body region, for which the implant is intended, is preferably to be provided here. In particular, the image data can also represent the body region in a time-resolved manner, for instance a dynamic representation of a cardiac movement, if for example the implant is intended as a supporting structure in a coronary vessel or as a cardiac valve.

Field markers which can in particular also be positioned manually can also be used for the segmentation. The segmentation is also preferably assisted by learning algorithms, so that e.g. for the segmentation a classification of the image data into regions of a known pattern takes place first and regions which at first do not correspond to any known pattern are classified manually, wherein the pattern recognition "learns" the corresponding classification.

An implant here may also comprise any implantation aids used for the implantation that are directly connected to the implant prior to implantation. The definition of the shape of the implant can take place in particular by the surface of a structure which corresponds to a segmented region being calculated. The implant can then at least partially have a negative mold with respect to the surface of the structure identified by segmentation. In particular, a shape of the implant can be predetermined by a calculation, which can still be manually adjusted prior to determining the or each interaction with the respective structure.

The interaction of the at least one structure with the implant comprises in particular a stress on the implant caused by the structure and a stress on the structure caused by the implant.

At least one embodiment of the invention is first based here on the consideration that a patient-specific adjustment of an implant to the individual anatomical conditions is most likely to be effected by the use of image data of the relevant body region of the patient. It is apparent here that the spatial resolution of the body region, which is available from the image data, can be used directly to define a shape of the implant, if regions which correspond in each case to structures of a different tissue can be segmented in the image data in each case. The segmentation of the individual regions allows a model of the body region to be created, which enables a definition of the shape of the implant by assigning individual pixels in a region, for which the implant is intended, to their position information. This type of definition of the geometry of the implant by way of the position information of pixels from image data allows a final shape as a manufacturing model also to be easily translated into a data format which can be read directly by a manufacturing machine so that it can manufacture the implant directly.

In a further step, it is now apparent that, for a structure which was already identified previously on the basis of the segmentation of its corresponding image regions in order to define the shape of the implant, an interaction with the implant can be determined in a patient-specific manner on the basis of the image data. During the construction of medical implants the possible stresses on the implant due to the surrounding tissue structures are at present calculated on the basis of standardized models. This at least allows possible stresses on the implant to be taken into account that could in the long term potentially result in signs of wear and tear. However, patient-specific changes to the relevant body region are not considered at all during the determination of the stresses.

However, precisely those body regions in which an implant is to be used for medical reasons often exhibit noticeable individual anatomical deviations from the standard given by a patient who is completely healthy in this body region. For instance vertebrae, between which an intervertebral disk is to be inserted, can be worn on one side due to a prolonged incorrect posture and resulting inappropriate stress, which would also be considered to be a cause of the damage to the intervertebral disk. If the extent of the wear is now not taken into account in the design of an intervertebral disk implant, the permanent inappropriate stress on the spinal column at this point cannot be corrected. An implant which only uses the degeneration of the vertebrae to be inferred from the image data statically for the definition of the shape, but not dynamically for the determination of the interaction of the vertebrae with the implant, is not optimally adjusted to the course of motions on account of the diverse movement pattern of the spinal column and the associated inadequate consideration of the effects of the patient-specific anatomical conditions produced here due to degeneration.

The result is on the one hand the risk of increased wear of the implant, which may make an early replacement of the implant necessary. This is undesirable on account of the operative intervention required. On the other hand an implant which is not optimally adjusted to the interactions can also place stress on the surrounding tissue structures. A body region into which an implant is inserted on account of a medical indication may as a result of the implant experience a temporary improvement in the condition that caused the indication. However, after some time the long-term stresses which the implant exerts on the surrounding tissue structures can on the one hand cause the medical indication to recur.

On the other hand, other indications such as tissue sclerosis or inflammations can also occur if the implant adversely subjects the tissue to long-term stress. With movable implants such as e.g. cardiac valves, a longer-term loss of optimal mobility also cannot be ruled out. In the worst case, an implant, in which the anatomical conditions of the patient are only taken into account statically to define the shape but not dynamically to determine possible stresses, could temporarily alleviate the symptoms of the medical indication requiring the implant, without however effectively eliminating their causes in the long term.

In contrast, it is now proposed to determine an interaction with the implant in a patient-specific manner for at least one structure on the basis of the segmented image data already present for the definition of the shape of the implant, and to check whether a predefined stress on the implant and/or on the structure is exceeded as a result of the interaction. If this is not the case, in other words if a predetermined stress limit is not exceeded for any of the checked structures during interaction with the implant, then the shape of the implant is accepted as a permissible manufacturing model and can be stored on a non-transitory data carrier or output by way of an interface for further processing, in particular for translation into a constructional language which can be read by a manufacturing machine.

It has proven advantageous for a model of the body region shown to be created from the segmented regions of the image data. The segmented regions correspond here to the structures of different tissue. The model here is in particular a data model of the body region shown, which is used to determine the interaction of the at least one structure with the implant. In order to determine the said interaction, a model of the body region shown in the image data has proven to be particularly advantageous, since the interaction can thus be determined in a patient-specific manner. In this way, it is possible to avoid disadvantages which result due to standardized stress models for the implant, e.g. due to force vectors which are not optimally adjusted in the implant, which would result in a reaction in the surrounding tissue and thus permanent stresses with associated consequences such as irritations or inflammations.

Image data generated by at least one medical imaging method is preferably provided. In particular, the image data here represents a three-dimensional resolution of the relevant body region. The image data which can be provided by a conventional medical imaging method in most cases has a resolution which is good enough to perform the method, in particular to define the shape of the implant on the basis of the position data of the individual pixels.

In an advantageous embodiment of the invention, image data generated by at least two medical imaging methods in each case with a different modality is provided, wherein a set of first image data and a set of second image data are generated by a first modality and a second modality in each case. In particular, the at least two medical imaging methods here in each case have a different resolution capability in respect of different structures of different body tissue so that the first image data in particular particularly effectively resolves at least a number of first structures and the second image data particularly effectively resolves at least a number of second structures. The quality of the resolution can be provided here for instance by the signal-to-noise ratio or the image contrast. In particular, the at least two medical imaging methods here comprise an MRT and a CT, with the structures effectively resolved by the MRT comprising soft tissue and the structures effectively resolved by the CT comprising bone tissue. This is advantageous in order to be able to determine interactions of the implant with a number of structures of different tissue.

In the first image data a number of regions which correspond to structures and in the second image data a number of regions which correspond to structures are expediently segmented here respectively, wherein a model of the body region shown is created from the regions of the first image data and the regions of the second image data. By using image data with different modalities, the model of the body region can represent the different structures of different tissue, which are effectively resolved in each case by different modalities, in particularly exact detail. The quality of the determination of the stress can be improved here by the or each interaction.

A shape of the implant is favorably defined by a predefined template being selected and the shape of the template being modified in a patient-specific manner on the basis of the image data. The template can in particular be superimposed here with a patient-specific data model of the relevant body region and adjusted on the basis of the segmented regions. An at least partially manual adjustment, which uses the graphical representation on a monitor, is also included here. The use of a predetermined template, which is individually adjusted to the anatomy of the patient, allows for the fact that implants of the same type often only deviate by a few percent (with respect to the overall volume of the implant) from a basic shape determined by the average anatomy. These deviations are however often essential to the correct medical function of the implant in the body region of the patient.

The use of such a basic shape as a template and its adjustment now allows the definition of the shape to be configured in a less compute-intensive manner, since only the patient-specific deviations from the basic shape have still to be calculated, and no longer the entire implant. Since the selection of the template can take place by way of simple pattern recognition for instance, this allows the compute-intensive part of the definition of the shape to be restricted to a few percent of the volume of the implant.

In a further advantageous embodiment of the invention, the interaction with the implant is determined for the at least one structure by a numerical simulation. A data model of the body region, for which the implant is intended, is preferably used for the simulation. In particular, the simulation can dynamically determine the stresses produced by the interaction of the implant with the relevant structures, i.e. that the stresses occurring during different movements of the body region are simulated here as part of a stress model forming the basis of the simulation.

A blood flow is additionally preferably simulated here in the simulation. This is particularly advantageous in the case of an implant intended for a blood vessel or as a cardiac valve.

Parameters for a critical stress are favorably predetermined for the definition of the manufacturing model for a number of areas of the implant and/or a number of areas of the at least one structure in each case and are compared in areas to a stress determined by the simulated interaction. In particular, position-dependent parameter functions can be predetermined here for the or each area in each case and as a function of its position coordinates the respective parameter function can be compared to the stresses determined for this by the simulation. A procedure of this type makes it possible in particular to determine, for an existing shape of the implant, the value by which at a certain point on the implant a permissible stress is exceeded. This information can then be used for the adjustment. In particular, the values determined by the simulation for the respective position-dependent stress on the implant and on the surrounding structures can be used to determine the locally occurring forces.

In a further advantageous embodiment of the invention, provision is made for the shape of the implant to be changed if the predefined critical stress is exceeded due to at least one interaction of the implant with a structure, wherein the interaction of the implant with the structure is determined again on the basis of the changed shape of the implant. This process can in particular be iterated. If the predefined critical stress is now no longer exceeded for the relevant structure, in particular for at least one, preferably for all adjacent structures, the current shape of the implant can be defined as a manufacturing model and the manufacturing model can be stored on a non-transitory data carrier and/or output by way of an interface.

Deviations, in areas, of a stress determined by a simulated interaction from a predefined critical stress are preferably used here to change the shape of the implant in each case. The change in the shape can be performed here particularly at areas where the predetermined values for the critical stress are exceeded significantly. The calculations for a redefinition of the shape can be implemented here in a more computationally-efficient manner.

A local density and/or a local material selection of the implant is preferably changed if the predefined critical stress is exceeded by at least one interaction of the implant with a structure, wherein the interaction of the implant with the structure is determined again on the basis of the changed local density and/or local material selection of the implant. This process can in particular be iterated. If the predefined critical stress is now no longer exceeded for the relevant structure, in particular for all adjacent structures, the current local density and/or local material selection of the implant can be defined as properties of the manufacturing model and the manufacturing model can be stored on a non-transitory data carrier and/or output by way of an interface.

At least one embodiment of the invention further specifies an apparatus which is set up to perform the method described above for generating a manufacturing model. This comprises in particular a processor or computer, which can be configured in particular with at least one ASIC designed especially for this purpose. The advantages specified for the method and its developments can be analogously transferred to the apparatus.

At least one embodiment of the invention moreover specifies a computer program with program code for performing the method described above for generating a manufacturing model, when the computer program is run on a computer.

At least one embodiment of the invention also specifies a method for producing a medical implant, which has method steps firstly comprising the generation of a manufacturing model via a method as described above, secondly the generation of a construction program which can be read by a producing apparatus on the basis of the manufacturing model and thirdly the generation of the implant in the producing apparatus on the basis of the construction program. One particular advantage here is that the manufacturing model can be output by the method for generation in a data format, which has a matrix-like three-dimensional volume representation of the implant, such as e.g. a CAD file.

Such a representation can be translated directly for a plurality of producing apparatuses, thus for instance for a 3D printer or a milling machine, into a construction program which can be read by the apparatus, which can comprise the instructions for the apparatus which are necessary for manufacture such as, in the case of the 3D printer, a file in the .stl format. A high probability of the manufacturing model output and a practical usability are thus ensured. Particularly with an output in an advantageous file format, the generation of the manufacturing model can be separated from the material production of the implant, which can contribute to simplifying the manufacture.

FIG. 1 shows in a block diagram a schematic representation of a method 1 for generating a manufacturing model 2 for a medical implant. In the present case, a set of first image data 6 and a set of second image data 8 are provided by two medical imaging methods CT, MRT, which are provided here by a computed tomography system CT and a magnetic resonance tomography system MRT. Another embodiment variant of the method 1 (not shown here), in which image data is provided by just one medical imaging method, has a comparable process flow. The first image data 6 and the second image data 8 are segmented separately from one another in each case. This means that in the individual image data associated regions 10, 12 are determined on the basis of certain homogeneity criteria, which in each case map structures 11, 13 with the same tissue. The regions 10 which are segmented in the first image data 6 provided by the CT correspond in the present case to structures 11 made of bone tissue, since this is particularly effectively resolved by the CT. The regions 12 which are segmented in the second image data 8 provided by the MRT accordingly map structures 13 of soft tissues of the relevant body region 14.

A virtual model 16 of the mapped body region 14 is now created from the regions 10 segmented in the first image data 6 and the regions 12 segmented in the second image data 8. A shape 18 for the implant to be manufactured is now defined on the basis of this model 16. The template which is as similar as possible to the implant to be manufactured in terms of its shape is first selected here from a number of predefined templates by way of pattern recognition in the model 16. The selected template 20 is then directly or indirectly modified in a patient-specific manner on the basis of the image data 6, 8, i.e. on the basis of the model 16 generated from the regions 10, 12 segmented therefrom. Within the scope of the model 16 or the image data 6, 8 from which it is generated, possible interactions 22 with the structures 11, 13 surrounding the implant are now determined in a numerical simulation 24 for the defined shape 18 of the implant. Here the simulation 24 calculates in a spatially-resolved manner on the basis of mechanical stress models the effects which an interaction 22 has on the implant with the shape 18 and on the surrounding structures 11, 13 during movements of the body region 14, and also determines respective local stress parameters 25.

If a predefined critical stress 26 is exceeded by the respective local stress parameter 25, then the shape 18 is modified on the basis of the local stress parameters 25 determined, in particular on the basis of the respective level of exceedance of the critical stress 26 by the local stress parameter 25, and the simulation 24 for the interactions 22 is performed again. This is now iterated until the critical stress 26 for the entire body region 14 and the implant remains unexceeded. The shape 18 of the implant thus determined as permissible is defined as a manufacturing model 2 for the implant and can now be stored on a non-transitory data carrier 30 or output by way of an interface 32.

Figure 2:
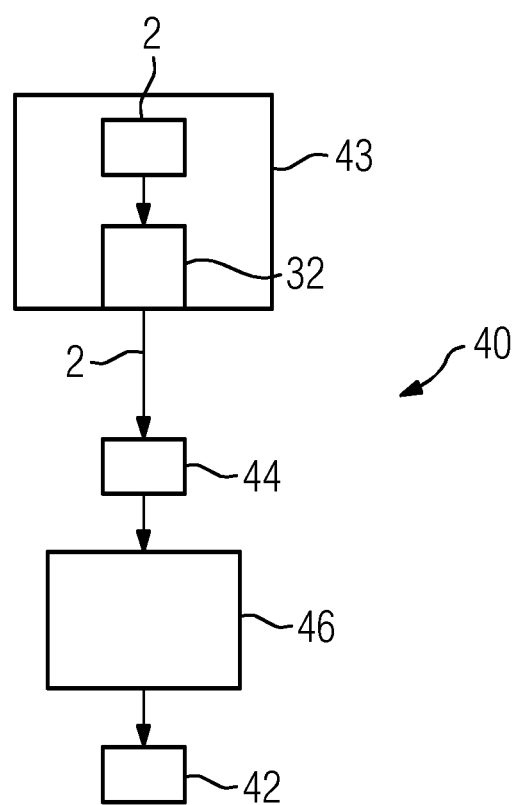

FIG. 2 shows a schematic representation in a block diagram of the process flow of a method 40 for manufacturing a medical implant 42 designed according to FIG. 1. According to the above-described method 1 shown in FIG. 1, a manufacturing model 2 for the implant 42 is generated on a computer 43 configured especially for this purpose and is output by way of an interface 32. The manufacturing model 2 is now translated into a construction program 44, which can be read directly by a producing apparatus, which is provided here by a 3D printer 46, in other words into a file in the. Stl format. The 3D printer 46 now generates the implant 42 on the basis of the construction program 44, which represents a direct implementation of the manufacturing model 2.

Figure 3:
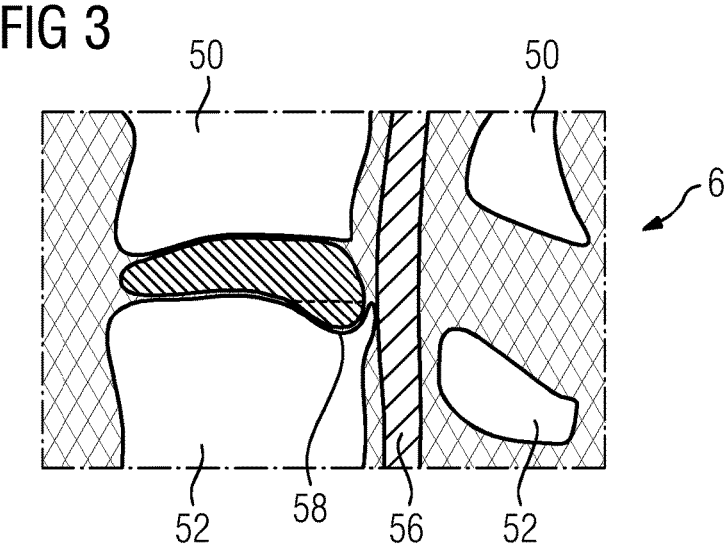
Figure 4:
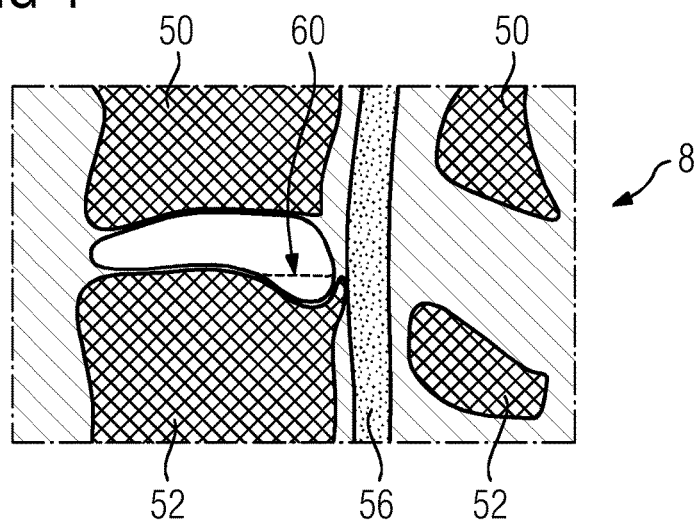

FIG. 3 and FIG. 4 each show schematic representations of the same longitudinal section plane of a cut-out of a spinal column in first image data 6 and in second image data 8, which map two vertebrae 50, 52 and an intermediate intervertebral disk 54. In the first image data 6 shown in FIG. 3, the two vertebrae 50, 52 are particularly easily identified by the high contrast, in the second image data 8 shown in FIG. 4, the intervertebral disk 54 and the underlying spinal cord 56 are better resolved. A slight protrusion 58 on the lower vertebra 52 can be seen in the first image data, said protrusion representing a deviation from a shape 60 of the same vertebra which is usually to be expected in an average person. For the sake of clarity, this usually expected shape 60 is shown with a dashed line and does not represent an integral part of the image data. Here the protrusion 58 may be congenital, or may have developed due to a long-standing incorrect posture or stress on account of degeneration. It is apparent in the second image data 8 that the spinal cord 56 passes the vertebrae 50, 52 in the vicinity of the protrusion 58.

Figure 5:
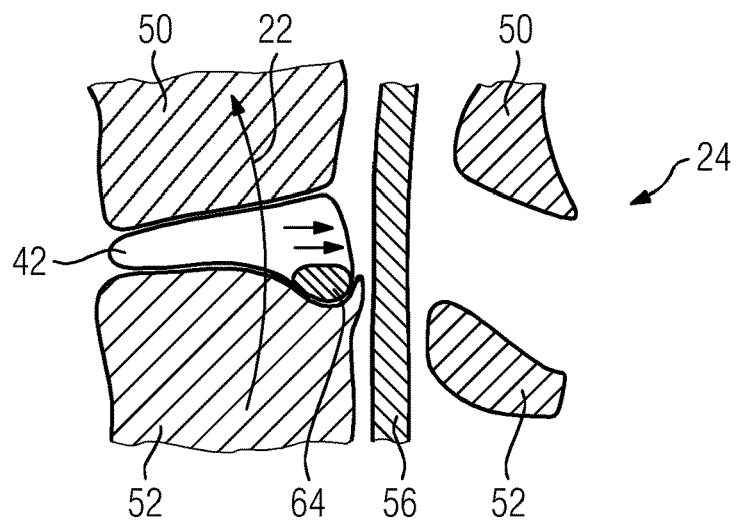

FIG. 5 shows a schematic representation of a simulation 24 of an interaction 22 of an implant 42 with the structures 11 that surround it. A model 16 of the corresponding body region, which comprises the vertebrae 50, 52, the intervertebral disk 54 and the spinal cord 58, has been produced here on the basis of the image data 6, 8 according to FIG. 3 and FIG. 4. The intervertebral disk 54 is now replaced in the model 16 for a numerical simulation 24 of the interaction 22 by the implant 42 with a predefined shape.

The interaction 22 consists here of a curvature of the spinal column. The stress on the implant 42 during the interaction 22 is now calculated in each case by the simulation 24 of the interaction 22. With a movement of the patient which results in the corresponding curvature of the spinal column, this determines that stronger forces in the direction of the spinal cord 56 act on the implant 42 on account of the protrusion 58 which represents an individual anatomical anomaly and a critical stress 26 in the area 64 of the implant is exceeded. In the long term, this can result either in a protrusion of the implant 42 or in its excessive wear and tear as a result of friction with the vertebrae 50, 52. In the present case, the shape of the implant 42 was adjusted on the basis of the knowledge obtained by the simulation 24, and the interaction 22 (and if necessary others) was again checked for critical stresses on the implant 42. If these are now no longer exceeded as a result of the changed shape of the implant 42, the thus defined shape of the implant 42 can be defined as a manufacturing model and output.

Figure 6:
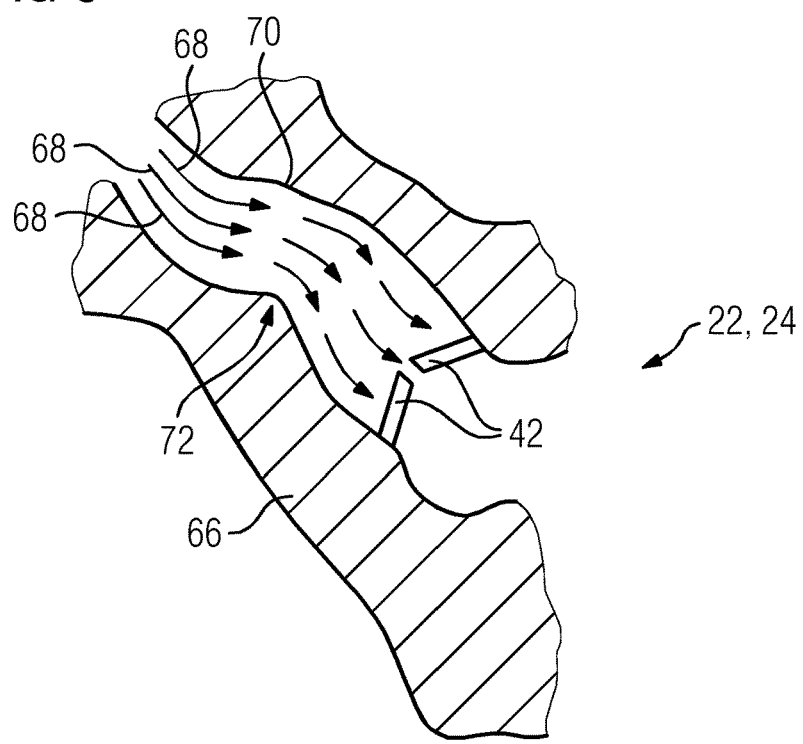

FIG. 6 shows a cross-sectional representation of a simulation 24 of an interaction 22 of a cardiac valve implant 42 with the surrounding tissue 66. The interaction 22 consists here essentially of the effects on the surrounding tissue 66 of opening and closing the cardiac valve implant 42. A blood flow 68 is taken into account here for the simulation 24. If the aorta 70, into which the implant 42 is to be inserted, has a constriction 72 for instance, then an excessively strong blood flow 68 in this region could increase the blood pressure for instance, which in the long term could cause sequelae in the patient. In the present case, the shape of the implant 42 can be adjusted to the requirements of the blood flow 68, which result from the individual anatomy of the patient, in particular his/her aorta 70.

Although the invention has been illustrated and described in more detail by the preferred example embodiment, the invention is not restricted by this example embodiment. Other variations can be derived herefrom by the person skilled in the art without departing from the scope of protection of the invention.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of manufacturing a medical implant based on a manufacturing model of the medical implant, the method comprising:
    providing image data of a body region;
    segmenting regions in the image data to generate segmented regions, each of the segmented regions respectively corresponding to structures of different tissue;
    defining a shape of the medical implant based on the segmented regions which correspond to the structures;
    determining a stress applied by the medical implant to at least one of the structures of a patient in a patient-specific manner based on the image data;
    checking, for the at least one of the structures, whether the stress exceeds a critical stress;
    defining the shape of the medical implant as the manufacturing model;
    upon the critical stress not being exceeded for each of the at least one of the structures, at least one of,
        storing the manufacturing model on a non-transitory data carrier, and
        outputting the manufacturing model via an interface to a producing apparatus;
    generating a construction program, readable by the producing apparatus based on the manufacturing model stored on the non-transitory data carrier or output to the producing apparatus via the interface; and
    generating the medical implant in the producing apparatus based on the construction program.

2. The method of claim 1, wherein the manufacturing model of the body region is created from the segmented regions of the image data.

3. The method of claim 2, further comprising:
    generating the image data by at least one medical imaging method.

4. The method of claim 3, further comprising:
    generating the image data by at least two medical imaging methods, each of a different modality, wherein first image data and second image data are respectively generated via a first modality and via a second modality.

5. The method of claim 4, wherein the segmenting includes segmenting a number of regions which respectively correspond to structures in the first image data, and segmenting a number of regions which respectively correspond to structures in the second image data and wherein the manufacturing model of the body region is created from the regions of the first image data and the regions of the second image data.

6. The method of claim 1, wherein
the shape of the medical implant is changed to a changed shape, if the critical stress is exceeded and
the stress of the medical implant is determined again based on the changed shape of the medical implant.

7. The method of claim 1, further comprising:
generating the image data by at least one medical imaging method.

8. The method of claim 7, further comprising:
generating the image data by at least two medical imaging methods, each of a different modality, wherein first image data and second image data are respectively generated via a first modality and via a second modality.

9. The method of claim 8, wherein the segmenting includes segmenting a number of regions which respectively correspond to structures in the first image data, and segmenting a number of regions which respectively correspond to structures in the second image data and wherein the manufacturing model of the body region is created from the regions of the first image data and the regions of the second image data.

10. The method of claim 1, wherein the shape of the medical implant is defined by a template being selected and the shape of the template being modified in a patient-specific manner based on the image data.

11. The method of claim 1, wherein the stress with the medical implant is determined for the at least one of the structures by a numerical simulation.

12. The method of claim 11, wherein a blood flow is also simulated in the numerical simulation.

13. The method of claim 12, wherein, in order to define the manufacturing model for at least one of a number of areas of the medical implant and a number of areas of the at least one structure, parameters are defined in each case for a critical stress and are compared in areas to a stress determined by the numerical simulation.

14. The method of claim 11, wherein, in order to define the manufacturing model for at least one of a number of areas of the medical implant and a number of areas of the at least one structure, parameters are defined in each case for a critical stress and are compared in areas to a stress determined by the numerical simulation.

15. The method of claim 14, wherein the shape of the medical implant is changed to a changed shape, if the critical stress is exceeded and wherein the stress applied by the medical implant is determined again based on the changed shape of the medical implant.

16. The method of claim 15, wherein deviations of a stress determined by a simulated interaction from a defined critical stress are respectively used in respective areas to change the shape of the medical implant.

17. The method of claim 1, wherein at least one of a local density and a local material selection of the medical implant is changed to a changed local density and a changed local material selection, respectively, if the critical stress is exceeded, and
wherein the stress applied by the medical implant is determined again based on at least one of the changed local density and the changed local material selection of the medical implant.

18. A non-transitory computer readable medium including program code, for performing the method of claim 1 when the program code is executed on a computer.

19. An apparatus for at least one of storing and outputting a manufacturing model for a medical implant, the apparatus comprising:
a processor configured to,
receive image data of a body region;
segment regions in the image data to generate segmented regions, each of the segmented regions respectively corresponding to structures of different tissue;
define a shape of the medical implant based on the segmented regions which correspond to the structures;
determine a stress applied by the medical implant to at least one of the structures of a patient in a patient-specific manner based on the image data;
check, the at least one of the structures, whether the stress exceeds a critical stress;
define the shape of the medical implant as the manufacturing model;
upon the critical stress not being exceeded for each of the at least one of the structures, the processor is configured to at least one of,
store the manufacturing model on a non-transitory data carrier, and
output the manufacturing model via an interface for generating a manufacturing model to a producing apparatus;
generate a construction program, readable by the producing apparatus, based on the manufacturing model stored on the non-transitory data carrier or output to the producing apparatus via the interface; and
generate the medical implant in the producing apparatus based on the construction program.

* * * * *